(12) United States Patent
Odderson

(10) Patent No.: US 7,558,610 B1
(45) Date of Patent: Jul. 7, 2009

(54) ELECTRIC DIAGNOSTIC TAPE MEASURE AND METHOD

(76) Inventor: Ib R. Odderson, 9319 NE. 135th La., Kirkland, WA (US) 98034

( * ) Notice: Subject to any disclaimer, the term of this patent is extended or adjusted under 35 U.S.C. 154(b) by 61 days.

(21) Appl. No.: 11/444,644

(22) Filed: May 31, 2006

Related U.S. Application Data

(60) Provisional application No. 60/686,331, filed on Jun. 1, 2005.

(51) Int. Cl.
*A61B 5/0492* (2006.01)
*A61B 5/053* (2006.01)

(52) U.S. Cl. .................. 600/384; 600/391; 600/547; 600/554

(58) Field of Classification Search .............. 600/372, 600/547, 554, 384, 391
See application file for complete search history.

(56) References Cited

U.S. PATENT DOCUMENTS

| | | | | |
|---|---|---|---|---|
| 5,042,481 A | * | 8/1991 | Suzuki et al. | 600/393 |
| 5,191,886 A | * | 3/1993 | Paeth et al. | 600/382 |
| 5,327,902 A | * | 7/1994 | Lemmen | 600/547 |
| 5,406,715 A | * | 4/1995 | Koizumi et al. | 33/706 |
| 5,518,007 A | * | 5/1996 | Becker | 600/390 |
| 7,283,869 B2 | * | 10/2007 | Onda et al. | 600/547 |
| 2004/0236202 A1 | * | 11/2004 | Burton | 600/384 |
| 2005/0148898 A1 | * | 7/2005 | Odderson | 600/544 |
| 2006/0253167 A1 | * | 11/2006 | Kurtz et al. | 607/48 |

* cited by examiner

*Primary Examiner*—Lee S Cohen
(74) *Attorney, Agent, or Firm*—Dean A Craine

(57) ABSTRACT

An electric diagnostic tape measure used to measure the electrical conduction of a peripheral nerve using a standard electrical nerve stimulator. The tape measure includes a flexible, elongated body with an active recording electrode mounted or attached to its distal end. Formed on the lower surface of the active recording electrode is a conductive, adhesive layer that temporarily holds the electrode on the patient's skin during a test. Located on the top surface of the elongated body is a distance-measuring index. During a test, the elongated body is aligned so that the end of the distance-measuring index is aligned and registered with the active recording electrode. By moving the nerve stimulator to different locations adjacent to the skin adjacent to the elongated body, the distance of the nerve being tested may be measured. In one embodiment, a wire extends through the elongated body.

13 Claims, 6 Drawing Sheets

US 7,558,610 B1

ELECTRIC DIAGNOSTIC TAPE MEASURE AND METHOD

This is a utility patent application which claims benefit of U.S. provisional application No. 60/686,331 filed on Jun. 1, 2005.

BACKGROUND OF THE INVENTION

1. Field of the Invention

This invention relates to devices for measuring nerve conduction in peripheral nerves and more particularly, to such devices that measure the conduction time and amplitude of a test signal applied to a peripheral nerve.

2. Description of the Related Art

It is common practice in medicine to measure the electrical conduction on a peripheral nerve. A common use of this test is diagnosing carpel tunnel syndrome when electrical conduction in the median nerve is measured across the wrist. During the test, the physician measures the conduction time and the amplitude (compound muscle action potential or sensory nerve action potential) of the nerve by stimulating the nerve with a nerve stimulator. When setting up for the test, the active recording electrode and a second electrode, called reference recording electrode is attached to the patient's skin over the nerve or the muscle activated nerve. A ground-recording electrode is attached nearby to the skin. The nerve stimulator is then applied to the skin at a pre-measured distance from the active recording electrode.

When testing for carpel tunnel syndrome, the active and reference recording electrodes and the nerve stimulator's cathode probe are spaced apart over the hand and forearm at several known distances (8 cm, 10 cm, and 14 cm). Heretofore, physicians have used a ruler and an ink marker to first mark the specific locations on the forearm where the active recording electrode and the stimulator's cathode probe should be placed during the test. Often, several tests are performed that requires manually marking several sets of reference points on the skin. The act of measuring and marking several sets of reference points on the forearm and hand is very time consuming. Also, because the sets of marked points are relatively close, a wrong set of reference points may be used during the test that produces inaccurate readings.

SUMMARY OF THE INVENTION

It is an object of the present invention to provide an electrical diagnostic tape measure that enables a physician to easily and quickly determine the distance between the active recording electrode and the nerve stimulator's cathode probe.

It is another object of the invention to provide such a device that enables the physician to easily move the nerve stimulator to different locations over the nerve and then easily measure the distance between the active recording electrode and the stimulator's cathode probe.

These and other objects are met by an electrical diagnostic tape measure disclosed herein used to measure the distance between the active recording electrode and the cathode probe on a nerve stimulator placed at different locations over the nerve or muscle. The tape measure includes a flexible, elongated body with the active recording electrode attached to its distal end. Attached to the bottom surface of the active recording electrode is a conductive adhesive layer that temporarily holds the active recording electrode on the patient's skin. A strip of protective tape is placed over the conductive adhesive layer, which is removed just prior to use.

Printed on one surface of the elongated body is a distance-measuring index. The end of the distance-measuring index is aligned and registered with the center axis on the active recording electrode so the distance between the active recording electrode and the stimulator cathode prong placed at different locations on the skin next to the elongated body may be easily determined. In the preferred embodiment, an electric wire extends through the elongated body and connects at one end to the active recording electrode. The proximal end of the wire extends from the opposite end of the elongated body and eventually connects to the terminal on the recording machine.

In one embodiment, the active recording electrode and a reference electrode are both longitudinally aligned and securely attached to the distal end of the elongated body. In another embodiment, both electrodes are removably attached to the elongated body to allow the physician or technician to individually place them at different positions along the elongated body or at different locations on the patient's skin.

Using the above tape measure, a method for measuring peripheral nerve conduction is also provided.

DESCRIPTION OF THE PREFERRED EMBODIMENT(S)

Figure 1:
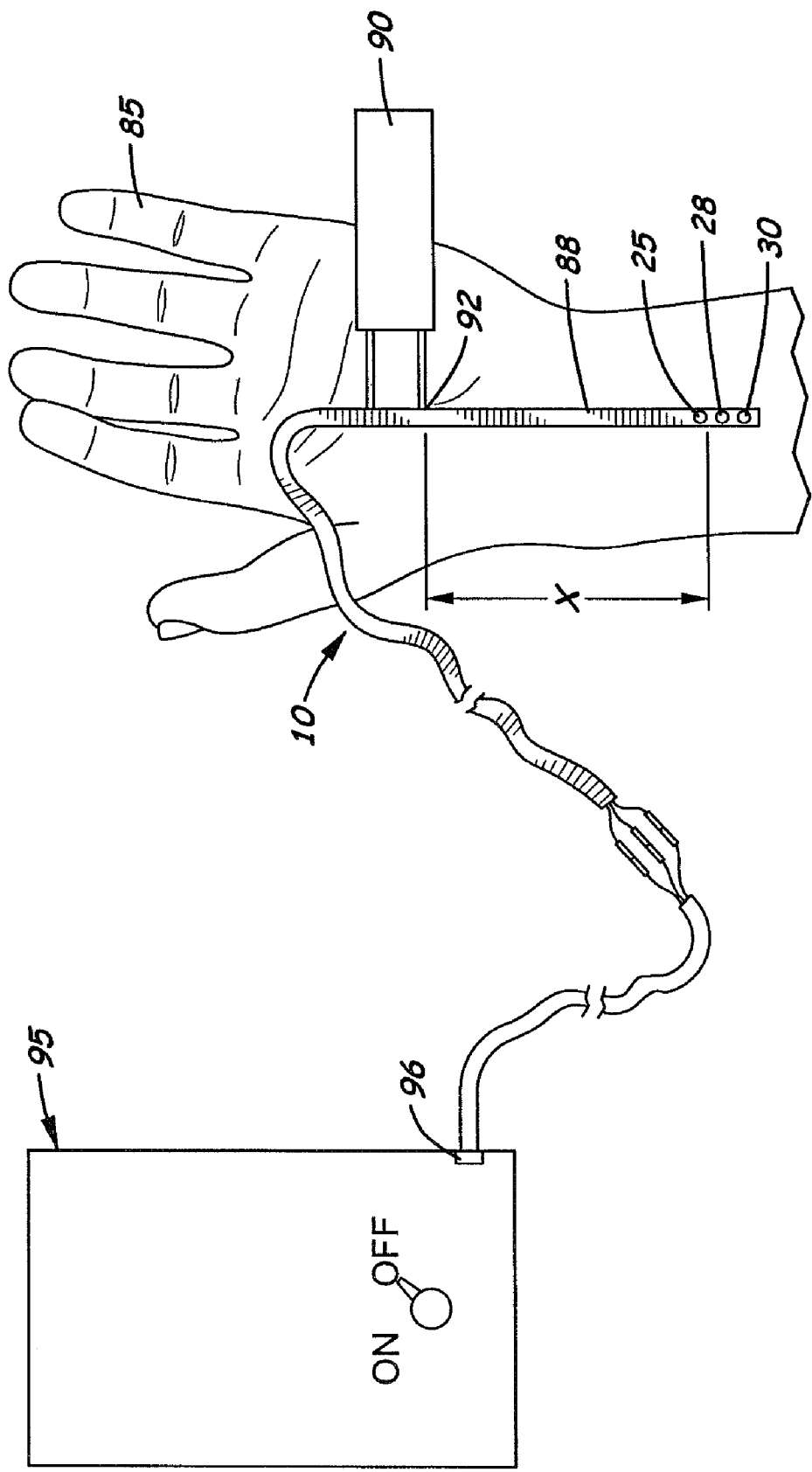
FIG. 1 is an illustration showing the first embodiment of the tape measure disclosed herein, located on over the palm of a user's right hand, to measure conduction along a sensory nerve in the forearm and hand with a nerve stimulator placed over the palm at a known distance as indicated on the tape measure.
Figure 2A:
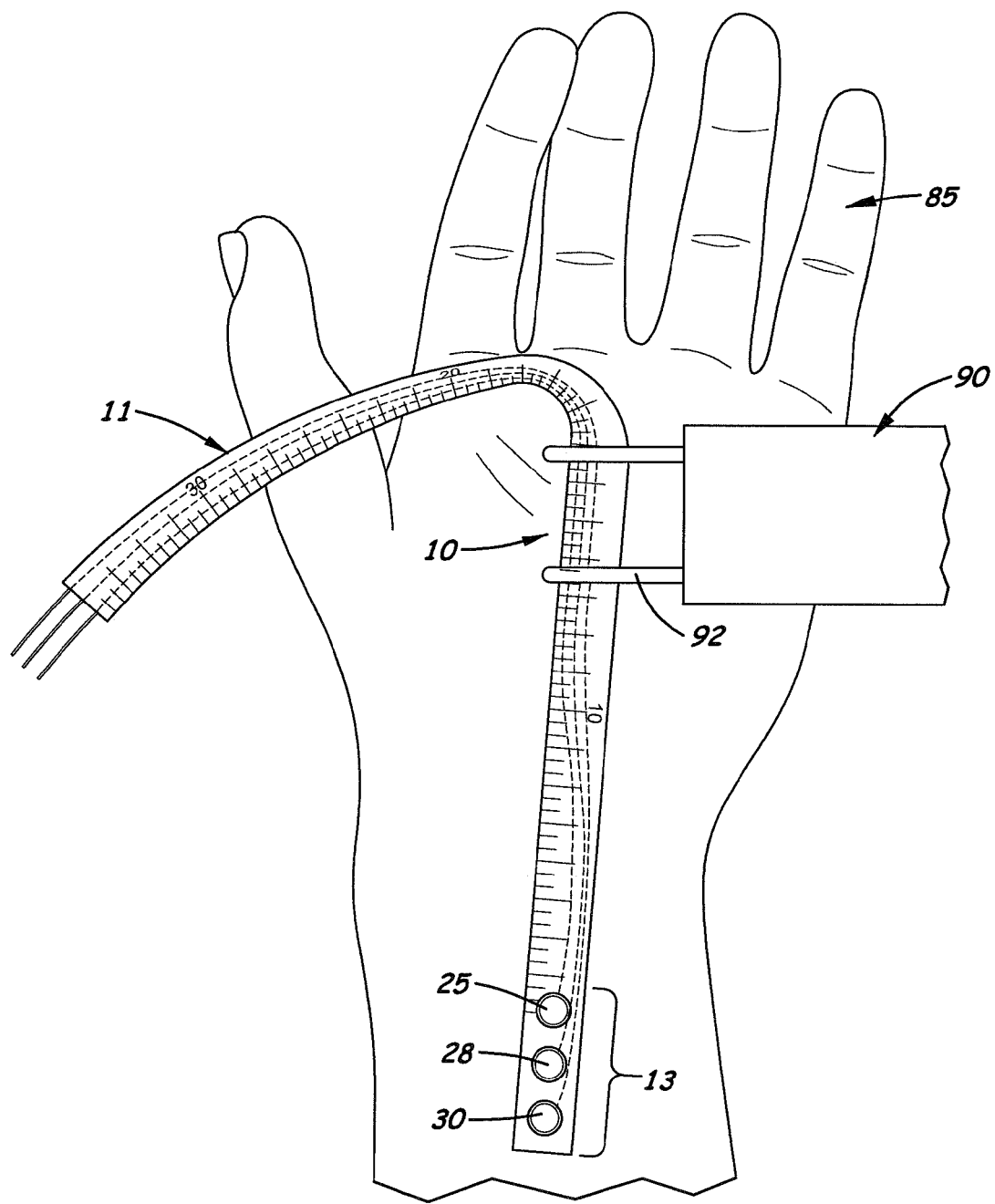
FIG. 2A is an enlarged illustration of the tape measure and nerve stimulator shown in FIG. 1.
Figure 2B:
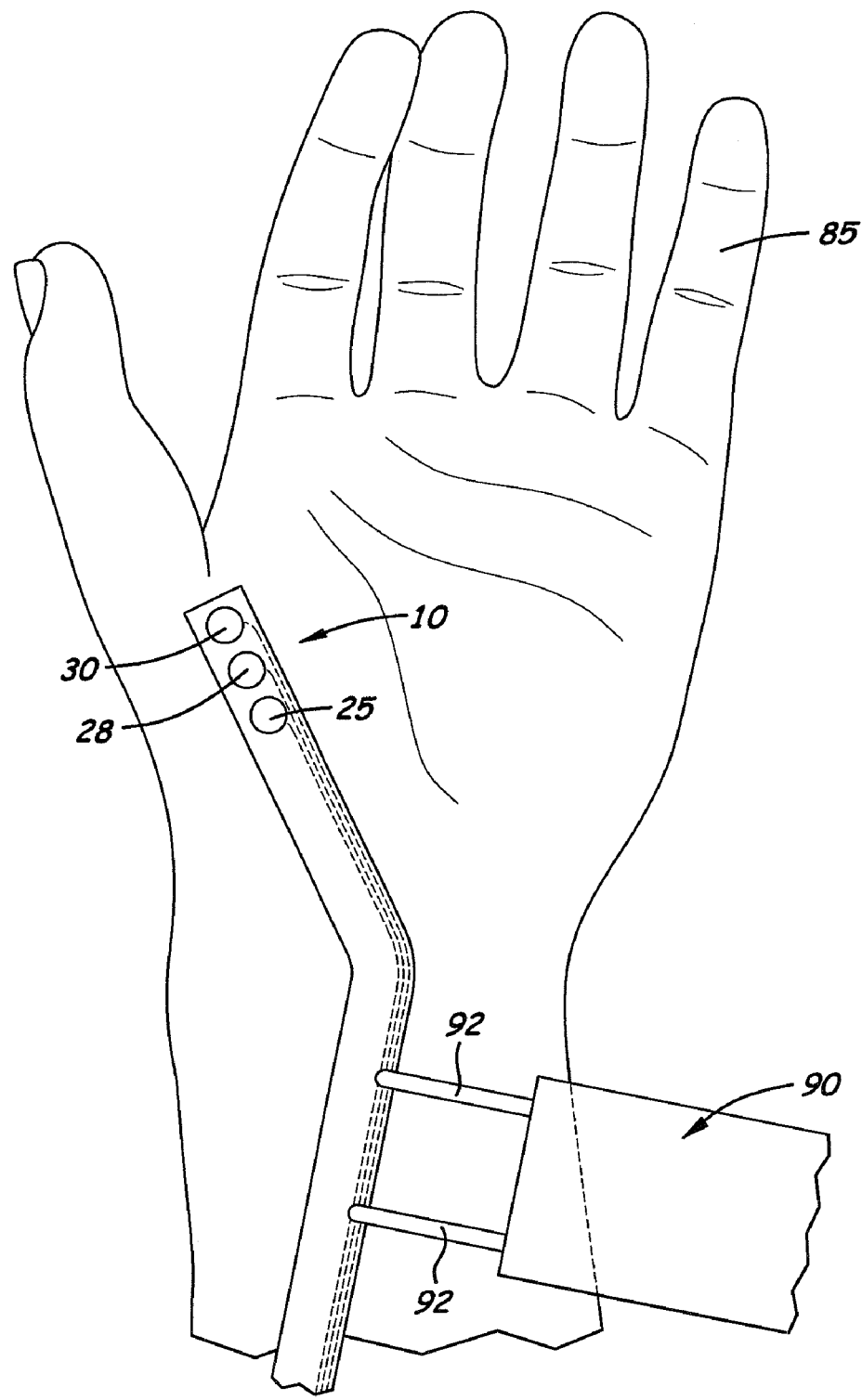
FIG. 2B is an illustration similar to the illustration shown in FIG. 2A showing the tape measure rotated over the forearm and palm with the nerve stimulator being placed on the forearm to test the electrical conduction of a motor nerve.

Referring to the accompanying FIGS. 1-2A, 2B there is shown a nerve conduction electrical diagnostic tape measure 10 used to measure the distance between the cathode probe 92 on a nerve stimulator 95 and the active recording electrode 25 attached to a recording device 95. By moving the cathode probe 92 to different locations over the nerve 88 on the hand 85, the distance between the cathode probe 92 and the active recording electrode 25 may be changed, thereby enabling nerve conduction studies to be completed.

The tape measure 10 includes a flexible, elongated body 11 with an active electrode 25 attached to its distal end 13. Attached to the bottom surface of the active recording electrode 25 is an adhesive layer 40 that temporarily holds the active recording electrode 25 on the patient's skin.

Printed on the top surface 15 of the elongated body 11 is a distance-measuring index 20. The end of the distance-measuring index 20 is aligned and registered with the center axis and the active recording electrode 25. In the preferred embodiment, an electrical wire 50 extends longitudinally through the elongated body 11. The distal end 52 of the electrical wire 50 connects to the active recording electrode 25 while the opposite proximal end 54 connects to a suitable connector 60 directly or indirectly attaches to the terminal 96 on a recording device 95.

FIGS. 1, 2A, 2B and 3A show a first embodiment on the invention in which the active recording electrode 25, a reference electrode 28 and a ground electrode 30 all longitudinally aligned and attached to the distal end 13 of the elongated body 11.

Figure 3A:
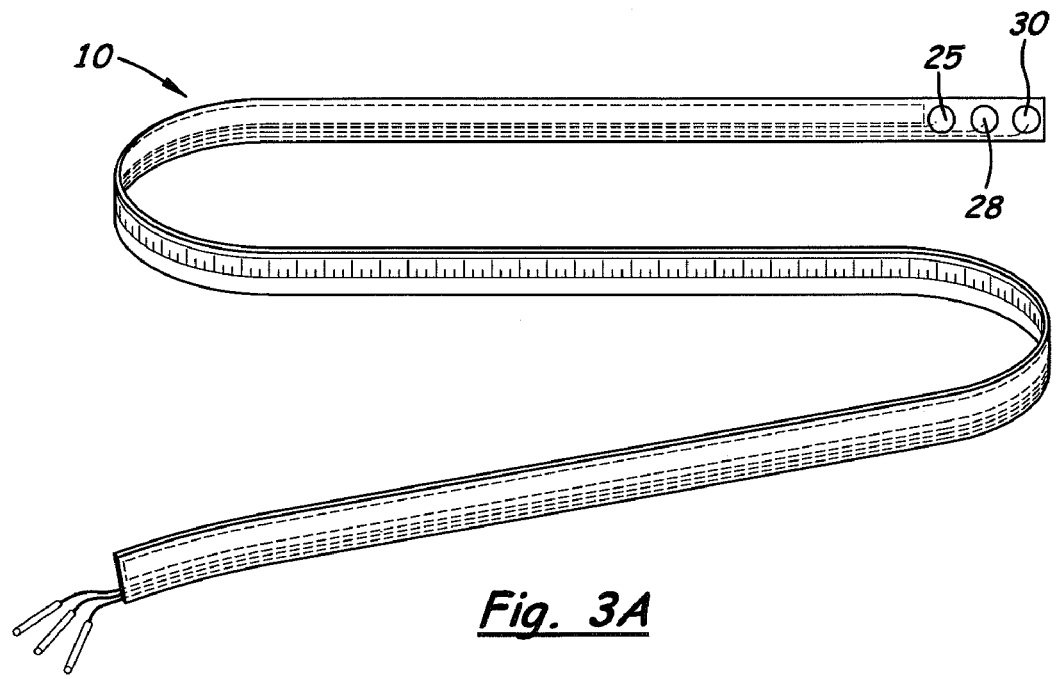
FIG. 3A is a perspective view of the first embodiment of the tape measure with the active, reference and ground electrodes being longitudinally aligned and permanently attached to the distal end of the elongated body and three separate electric wires being extended along the elongated body.
Figure 3B:
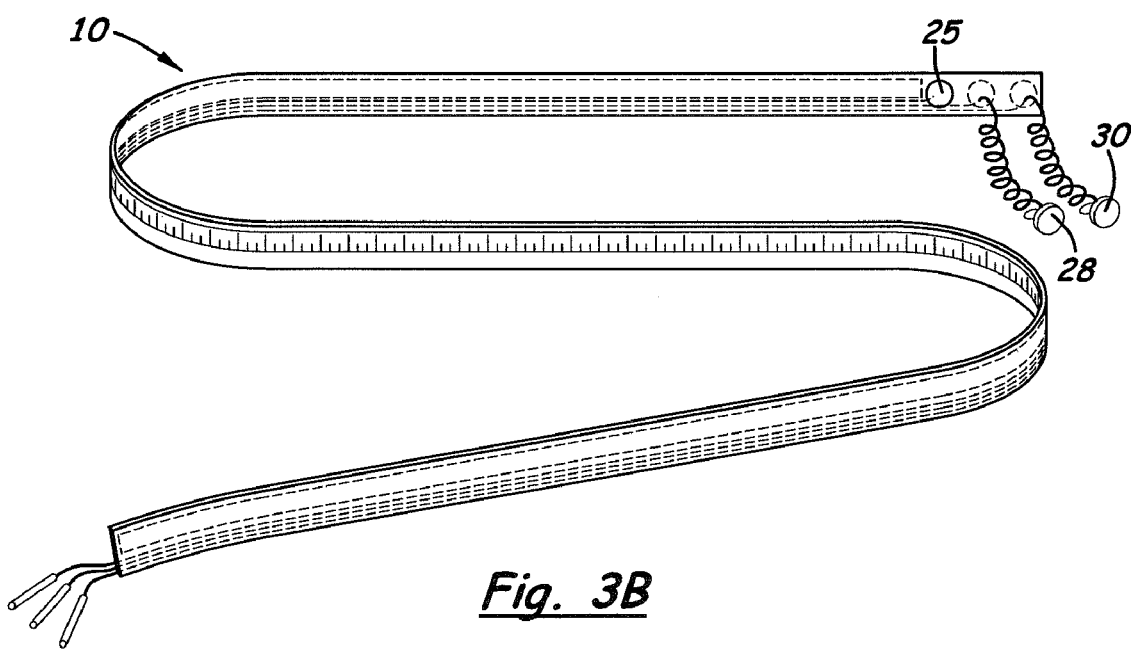
FIG. 3B is a perspective view of a second embodiment of the tape measure similar to the embodiment shown in FIG. 3A only with the active electrode being permanently attached and the reference and ground electrodes being removably attached to the distal end of the elongated body.

FIG. 3B is a perspective view showing the active recording electrode 25 permanently attached to the elongated body 11 and the reference and ground electrodes 28, 30, respectively being removably attached to the distal end 13 of the elongated body 11.

Figure 3C:
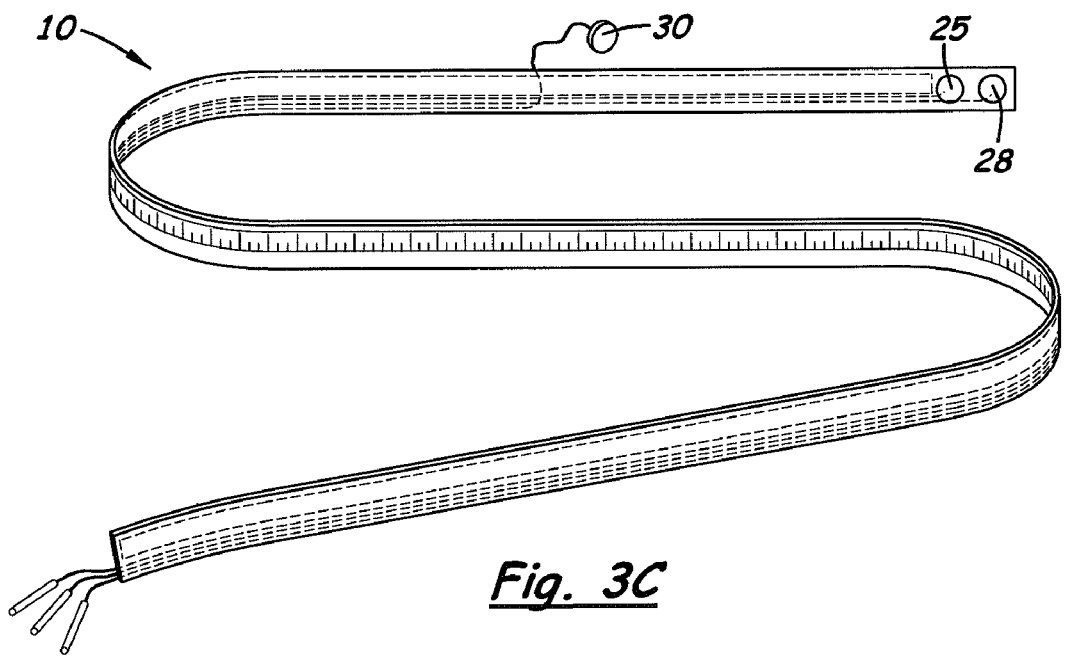
FIG. 3C is a perspective view of a third embodiment of the tape measure similar to the embodiments shown in FIGS. 3A and 3B with the active and reference electrodes permanently attached to the distal end of the elongated body and a detached ground electrode that is more likely to be used to test the electrical conduction of a motor nerve.

FIG. 3C shows a third embodiment of the invention in which the active and reference electrodes 25, 28, respectively, are longitudinally aligned and securely attached to the distal end 13 of the elongated body 11. The ground electrode 30 is a separate structure capable of being placed at any desired position on the skin.

Figure 3D:
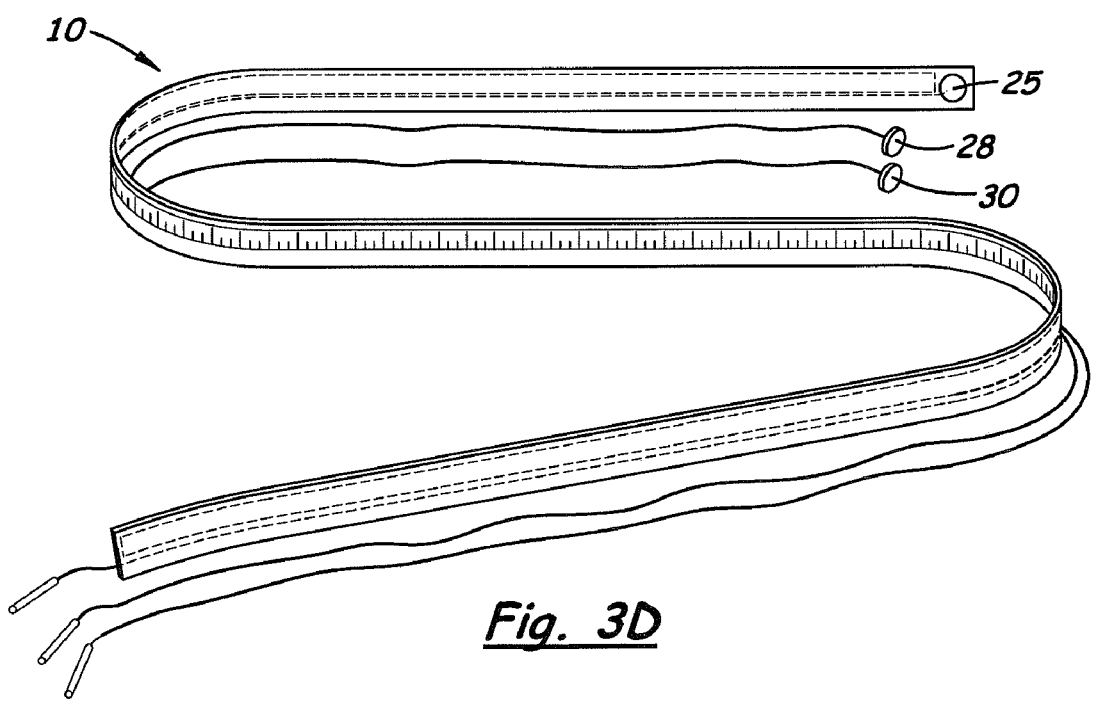
FIG. 3D is a perspective view of a fourth embodiment of the tape measure with the reference electrode permanently attached to the distal end of the elongated body while the active and ground electrodes and their wires being separate structures.

FIG. 3D shows a fourth embodiment of the invention in which the reference electrode 28, the ground electrode 30, and wires connecting 36, 38, respectfully, are separate structures from the elongated body 11 and only the active recording electrode 25 is attached at the distal end 13 of the elongated body 11. With this embodiment, the physician is able to adjust the position of the reference and ground electrodes 28, 30 with respect to the active recording electrode 25.

Figure 4:
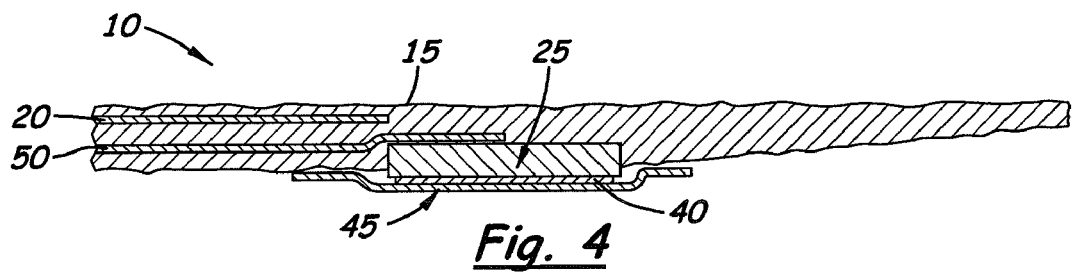
FIG. 4 is a sectional, side elevational view of the fifth embodiment of the tape measure showing one active electrode permanently attached to the distal end of the tape measure with an adhesive conductive layer placed over the lower surface of the active electrode and a protective strip of tape covering the conductive layer.

FIG. 4 is a sectional, side elevational view of a fifth embodiment of the invention showing a strip of removal protection layer 45 placed over the conductive adhesive layer 40 on the active recording electrode 25 to prevent the adhesive layer 40 from attaching to other surfaces.

Figure 5:
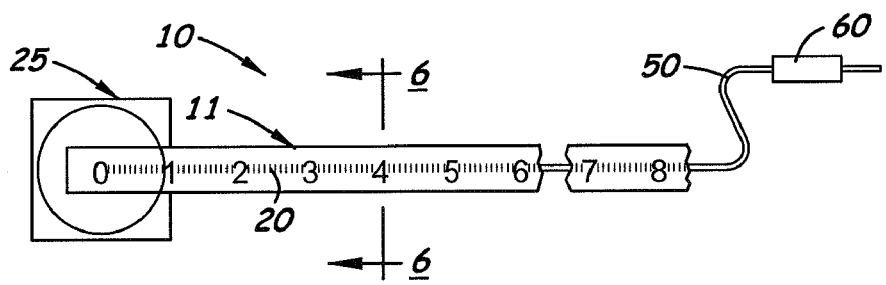
FIG. 5 is a top plan view of a sixth embodiment of the invention showing a circular active electrode attached to the distal end of an elongated body circular.
Figure 6:
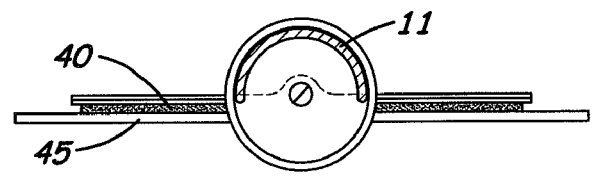
FIG. 6 is a sectional side elevational view taken along line 6-6 in FIG. 5.

FIGS. 5 and 6 are top plan and sectional, side elevational views, respectively, of a sixth embodiment of the invention in which the active recording electrode 25 is permanently attached to the distal end and the electrical wire 50 extends through the elongated body 11. Attached to the distal end of the elongated body 11 is a circular adhesive button 26 covered by a removable, square protective layer 45.

Figure 7:
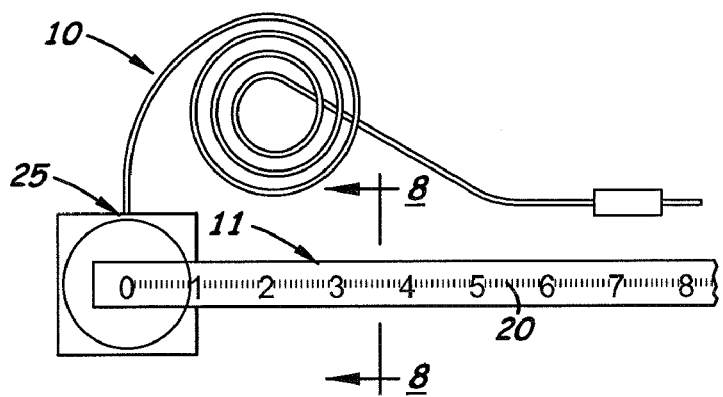
FIG. 7 is a top plan view of a seventh embodiment of the invention showing the active electrode attached to the distal end of the elongated body with the connecting wire detached from the elongated body.
Figure 8:
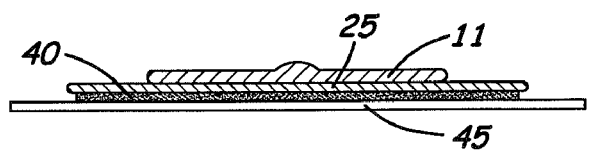
FIG. 8 is a sectional side elevational view taken along line 8-8 in FIG. 7.

FIGS. 7 and 8 are top plan and sectional, side elevational views, respectively, of a seventh embodiment of the invention similar to the embodiment shown in FIGS. 5 and 6 in which the active recording electrode 25 is permanently attached to the distal end of the elongated body 11 and the electrical wire 50 is disposed outside of the elongated body 11.

Using the above described tape measure, a method of testing peripheral nerve conduction is also provided comprising the following steps:

a. selecting a tape measure 10 comprising an elongated body 11 with a distance measuring index 20 printed thereon, said elongated body 11 including at least one recording electrode 25 located at one end and an electrical wire 50 that connects at one end to said recording electrode 25;

b. positioning said elongated body 11 on the skin directly over a peripheral nerve to be tested for conduction;

c. attaching said reference electrode 28 and said ground electrode 30 to a the skin near said nerve;

d. placing a nerve stimulator on the skin adjacent to said elongated body 11;

e. identifying the distance measurement index 20 on said elongated body 11; and;

f. activating the nerve stimulator to measure conductivity to said nerve.

In compliance with the statute, the invention described herein has been described in language more or less specific as to structural features. It should be understood, however, that the invention is not limited to the specific features shown, since the means and construction shown is comprised only of the preferred embodiments for putting the invention into effect. The invention is therefore claimed in any of its forms or modifications within the legitimate and valid scope of the amended claims, appropriately interpreted in accordance with the doctrine of equivalents.

I claim:

1. A peripheral nerve tape measure, comprising;
   a. a flexible elongated body, that includes a top surface, a bottom surface, a proximal end and a distal end;
   b. a first recording electrode located on or near said distal end of said elongated body, said recording electrode including a bottom surface with a skin compatible adhesive layer located thereon enabling said recording electrode to be attached to the skin;
   c. a distance measuring index extending over the entire length of said top surface from said first recording electrode to said proximal end of said elongated body; and,
   d. an electrical wire connected at one end to said first recording electrode.

2. The peripheral nerve tape measure, as recited in claim 1, further including a reference electrode attached to said elongated body near said distal end.

3. The peripheral nerve tape measure, as recited in claim 2, wherein said reference electrode is longitudinally aligned with said first recording electrode.

4. The peripheral nerve tape measure, as recited in claim 3, further including a ground electrode attached to said elongated body.

5. The peripheral nerve tape measure, as recited in claim 4, wherein said first recording electrode, said reference electrode and said ground electrode are longitudinally aligned on said elongated body.

6. The peripheral nerve tape measure, as recited claim 4, wherein said ground electrode is removably attached to said elongated body.

7. The peripheral nerve tape measure, as recited in claim 2, wherein said reference electrode is removably attached to said elongated body.

8. The peripheral nerve tape measure, as recited in claim 1, further including a ground electrode attached to said elongated body.

9. The peripheral nerve tape measure, as recited in claim 1, wherein said electrical wire extends longitudinally on said elongated body.

10. The peripheral nerve tape measure, as recited in claim 1, further including a removable protective layer placed over said adhesive layer.

11. The peripheral nerve tape measure, as recited in claim 1 wherein said adhesive layer is a circular tab covered by a square removable protective layer.

12. The peripheral nerve tape measure, as recited in claim 1, wherein said elongated body is tubular.

13. A method for measuring nerve condition in peripheral nerves comprising the following steps:
   a. selecting a tape measure comprising an elongated body with a distance measuring index printed thereon, said elongated body including at least one recording electrode located at one end and an electrical wire that connects at one end to said recording electrode;
   b. positioning said elongated body on the skin directly over a peripheral nerve to be tested;
   c. attaching the end of said electrical wire opposite the end connected to said recording electrode to a recording device;
   d. attaching a reference electrode and a ground electrode to the skin directly over the peripheral nerve to be tested;
   e. identifying the desired distance measurement index on said elongated body;
   f. placing a nerve stimulator on the skin adjacent to the desired distance measurement index; and,
   g. activating the nerve stimulator to measure the conductivity along said peripheral nerve.

* * * * *